US012788336B2

(12) United States Patent
Wilson

(10) Patent No.: US 12,788,336 B2
(45) Date of Patent: Nov. 10, 2026

(54) DEVICE AND METHOD FOR REDUCING RADIATION EXPOSURE FROM X-RAY TUBES

(71) Applicant: Egg Medical, Inc., Arden Hills, MN (US)

(72) Inventor: Robert F. Wilson, Roseville, MN (US)

(73) Assignee: Egg Medical, Inc., Arden Hills, MN (US)

( * ) Notice: Subject to any disclaimer, the term of this patent is extended or adjusted under 35 U.S.C. 154(b) by 188 days.

(21) Appl. No.: 17/904,194

(22) PCT Filed: Feb. 19, 2021

(86) PCT No.: PCT/US2021/018738
§ 371 (c)(1),
(2) Date: Aug. 12, 2022

(87) PCT Pub. No.: WO2021/168219
PCT Pub. Date: Aug. 26, 2021

(65) Prior Publication Data

US 2023/0120289 A1 Apr. 20, 2023

Related U.S. Application Data

(60) Provisional application No. 62/978,745, filed on Feb. 19, 2020.

(51) Int. Cl.
*A61B 6/10* (2006.01)
*A61B 6/00* (2006.01)

(52) U.S. Cl.
CPC ............ *A61B 6/107* (2013.01); *A61B 6/4441* (2013.01)

(58) Field of Classification Search
None
See application file for complete search history.

(56) References Cited

U.S. PATENT DOCUMENTS 5,075,045 A * 12/1991 Manchak, Jr. .......... G21F 9/008 264/257
5,604,784 A 2/1997 Widlicka et al.
6,483,719 B1 * 11/2002 Bachman ................ H05K 3/34 361/752
8,113,713 B2 2/2012 Belson et al.
(Continued)

FOREIGN PATENT DOCUMENTS

CA 3006471 A1 11/2019
CA 3098732 A1 12/2019
(Continued)

OTHER PUBLICATIONS

European Patent Office, Supplementary European Search Report dated Feb. 2, 2024 in European Patent Application No. 21757538.0, 13 pages.
(Continued)

*Primary Examiner* — Marcus H Taningco
(74) *Attorney, Agent, or Firm* — Inskeep IP Group, Inc.

(57) ABSTRACT

A radiation-absorbent shield shaped to conform to and enshroud the x-ray tube housing of a C-arm in order to protect medical personnel from radiation leaking through the x-ray tube housing. The shield is attached to the x-ray tube housing such that it moves with the tube housing and provides protection no matter the orientation of the C-arm.

14 Claims, 3 Drawing Sheets

(56) References Cited

U.S. PATENT DOCUMENTS

| | | | |
|---|---|---|---|
| 11,076,819 B2 | 8/2021 | Belson et al. | |
| 12,161,491 B2 | 12/2024 | Yifat et al. | |
| 2009/0232282 A1* | 9/2009 | Belson | A61B 6/4441 378/209 |
| 2016/0158082 A1* | 6/2016 | Gainor | A61B 6/0407 |
| 2017/0119324 A1* | 5/2017 | Wilson | G21F 3/00 |
| 2018/0025799 A1* | 1/2018 | Kim | G21F 1/12 250/515.1 |
| 2021/0098144 A1* | 4/2021 | Park | G21F 1/125 |
| 2021/0394427 A1* | 12/2021 | Frisco | B32B 27/308 |
| 2022/0233384 A1 | 7/2022 | Yadegari et al. | |

FOREIGN PATENT DOCUMENTS

| | | | |
|---|---|---|---|
| EP | 0220937 | A2 | 5/1987 |
| EP | 0220937 | A3 | 5/1987 |
| EP | 0777903 | B1 | 10/1998 |
| GB | 280636 | A | 11/1927 |
| JP | 2010-521992 | A | 7/2010 |
| JP | 2014041040 | A | 3/2014 |
| JP | 2015-225062 | A | 12/2015 |
| KR | 101783937 | B1 | 10/2017 |
| WO | WO 2008/048235 | A2 | 4/2008 |
| WO | WO 2008/048235 | A3 | 4/2008 |
| WO | WO 2008/140486 | A2 | 11/2008 |
| WO | WO 2019/227210 | A1 | 12/2019 |

OTHER PUBLICATIONS

Japanese Patent Office, Office Action dated Nov. 19, 2024 with English translation in Japanese Patent Application No. 2022-549639, 19 pages.

IP Australia, Examination Report No. 1 for standard patent application dated Nov. 3, 2025 in Australian Patent Application No. 2021224205, 4 pages.

* cited by examiner

DEVICE AND METHOD FOR REDUCING RADIATION EXPOSURE FROM X-RAY TUBES

RELATED APPLICATIONS

This application is the U.S. National Phase of and claims priority to International Patent Application No. PCT/US2021/018738, International Filing Date Feb. 19, 2021 entitled Device And Method For Reducing Radiation Exposure From X-Ray Tubes; which claims benefit of and priority to U.S. Provisional Application Ser. No. 62/978,745 filed Feb. 19, 2020 entitled Device For Reducing Radiation Exposure From X-Ray Tubes, both of which are hereby incorporated herein by reference in their entireties.

BACKGROUND OF THE INVENTION

X-rays for medical or industrial use are typically generated from an x-ray tube. In invasive radiology, cardiology, or vascular surgery laboratories, the x-ray tube is usually mounted in a tube housing located below the patient on a C-arm gantry. The patient lays on a table above the x-ray tube. An x-ray detector is located on the opposite side the C-arm, above the patient. X-rays generated by the tube are emitted through an aperture in the tube housing and pass through the patient to the detector.

The x-ray tube contains a cathode and an anode. The anode is typically composed of tungsten alloy. A large voltage difference applied between the cathode and anode causes electrons from the anode to accelerate into the tungsten cathode. These high energy electrons displace electrons in the tungsten atom, resulting in emission of high energy photons in the x-ray frequency spectrum. Typically, the energy of the photons varies from 30 keV to 110 keV. These photons are emitted in nearly all directions about the cathode. Many are reabsorbed by the cathode material (creating heat) and the remainder are radiated about the cathode. The typical x-ray tube is housed in a chamber which shields the emission of x-ray photons except for allowing the x-ray photons to emit through an aperture on the top of the housing.

During a procedure using an X-ray, health care workers are subjected to radiation from a variety of sources:

Scatter Radiation

A small minority of photons are transmitted are through the patient to the x-ray detector. The majority of x-ray photons emitted from the x-ray tube aperture interact with atoms in the air, x-ray table, and patient, and are re-emitted at all directions at lower energy (frequency). This secondary radiation is called scatter radiation. Scatter radiation is primarily through interaction of x-ray photons with electrons in the medium the photon is passing through. Elements have differing and characteristic x-ray interactions, but in the end, they scatter x-ray photons in all directions. The scattered photons (regardless of the mechanism of scatter) have less energy than the original photon.

The scattered photons are deflected from the path of the primary x-ray beam emitted from the tube housing aperture, causing internal radiation to body parts outside the primary beam and also radiation exposure to anyone around the patient. The intensity and energy level of the scatter radiation is dependent on the intensity and energy of the x-ray emitted from the tube housing, the amount and type of media the x-ray passes through (such as the type of tissue and the length of the path through the patient), and the individuals proximity to the primary beam path.

Scatter radiation is a significant health risk for healthcare workers in the x-ray room. Radiation exposure is associated with increased rate of cancer, cataracts in the eye, and hypertension. Workers typically use "lead aprons" around their body to block the harmful x-ray photons.

These factors have been quantitatively measured and are used to guide workers use of shielding devices. These devices, however, generally have a uniform level of protection not designed to match the energy level and scatter radiation pattern.

Leak from the x-Ray Tube Housing

It has been assumed that the vast majority of the x-ray exposure to healthcare workers is from scatter radiation from the patient, air, or x-ray table, and that x-ray photon leakage from the x-ray tube housing is negligible.

The Applicant has conducted testing on the effectiveness of the x-ray tube housing in blocking radiation from escaping the housing. Any leak from the housing is important because personnel in the room would be needlessly exposed to this radiation below the x-ray table. "Lead aprons" and other protective equipment typically stops at the knees or mid-calf, leaving the lower leg long bones, ankles, feet, muscles and skin exposed to substantial x-radiation.

The investigations showed that x-ray tube housings routinely leak significant levels of radiation. The radiation leak from the housing of the Philips Allura tube housing, for example, are shown below in Table 1.

TABLE 1

| Philips Allura | | | | | | | | | | | | | | | | | | |
|---|---|---|---|---|---|---|---|---|---|---|---|---|---|---|---|---|---|---|
| | Right | | | | Caudal | | | | | Left | | | | Cranial | | | | Average |
| | A | B | C | D | A | B | C | D | E | A | B | C | D | A | B | C | D | 1-4 |
| 1 | 828 | 1150 | 950 | 850 | 591 | 714 | 558 | 882 | 740 | 778 | 430 | 1470 | 729 | 602 | 730 | 920 | 437 | 786 |
| 2 | 196 | 1270 | 130 | 133 | 35 | 385 | 172 | 399 | 520 | 556 | 370 | 259 | 50 | 229 | 470 | 390 | 427 | 352 |
| 3 | 70 | 756 | 30 | 51 | 99 | 375 | 689 | 662 | 420 | 314 | 644 | 344 | 194 | 250 | 480 | 513 | 589 | 381 |
| 4 | 55 | 230 | 17 | 25 | 46 | 146 | 179 | 170 | 120 | 168 | 146 | 31 | 36 | 68 | 149 | 199 | 150 | 114 |
| 5 | 42 | 111 | 5 | 811 | 20 | 33 | | | | | 43 | 12 | 18 | | | | | 122 |
| Average (µSv/h) | 421 | | | | 395 | | | | | 407 | | | | 413 | | | | |

Further measurements demonstrate that the tube housing leak accounts for about 20% of all the radiation emitted or scattered below the x-ray table. Put into context, the average exposure of a worker standing next to a patient under fluoroscopy for a medical procedure varies from about 400 to 4000 μSv/h. Twenty percent of this radiation comes from the x-ray tube housing. This represents a substantial health risk to healthcare workers.

The average leak from the tube housing is not uniform across the surface of the housing. The leak in the Philips tube housing, for example, varies from approximately 20 to over 1,000 μSv/h. The average photon energy of the leak from the tube housing also varies from about 40-60 keV, depending on the location of the x-ray photon leak from the housing.

Shielding for x-ray photons exists and is widely used. These vary from garments worn by workers to shields that hang from the ceiling or table. However, none of these barriers move with the x-ray tube. Therefore, they must be positioned between the tube and the worker. Movement of the worker or the x-ray tube create a need to reposition the shield. Additionally, interruption of the radiation emission that was measured during the aforementioned investigations all around the tube housing would necessitate substantial shielding about the room.

As explained above, there is a significant need for a shielding system that can be used to prevent radiation leakage from an x-ray tube housing. There is also a need for a shielding system that moves with an x-ray tube, thus reducing the amount of stationary shielding in a room in order to adequately protect health care professionals.

OBJECTS AND SUMMARY OF THE INVENTION

The invention described herein, addresses the aforementioned need by providing a shielding system that surrounds an x-ray tube. The system is attached to, and moves with the tube such that the position of the tube, relative to the personnel and other objects in the room, is irrelevant. This greatly reduces both the radiation leaking through the tube and the scatter radiation that results from radiation leaking through the tube.

One embodiment of the invention provides a shield for reducing radiation leakage through an x-ray tube comprising a radiation-absorbent material shaped to enshroud an x-ray tube housing without obstructing an aperture thereof.

In at least one embodiment, the material of the shield has a laminar structure.

In at least one embodiment, the material of the shield has at least two layers.

In at least one embodiment, the material of the shield has at least one layer of a radio-opaque polymer joined to at least one layer of a flexible protective material.

In at least one embodiment, the shield includes a fastener usable to attach said shield to an x-ray tube housing.

In at least one embodiment, the shield further includes an adhesive for adhering the shield to an x-ray tube housing.

In at least one embodiment, the shield is made of a flexible material adapted to be wrapped around an x-ray housing and fastened to itself via a fastener, such as a hook and loop or other fastener.

One aspect of the invention is a method of reducing radiation exposure to health care workers present during an x-ray procedure involving covering surfaces of an x-ray tube housing with radiation-absorbent material.

In at least one embodiment, the method of the invention includes forming the radiation-absorbent material into a shape that is configured to enshroud the x-ray tube housing while not obstructing an x-ray aperture thereof and fastening the radiation-absorbent material to the x-ray tube housing.

In at least one embodiment, the method of the invention includes heating the radiation-absorbent material, applying the material to a form having said shape and allowing polymer layers of the radiation-absorbent material to fuse together.

In at least one embodiment, the method of the invention includes forming the radiation-absorbent material into a shape that is configured to enshroud the x-ray tube housing while not obstructing an x-ray aperture thereof involves applying the material to a form having said shape, heating the radiation-absorbent material, thereby causing the polymer layers of the radiation-absorbent material to fuse together in the desired shape.

In at least one embodiment, the method of the invention includes covering surfaces of the x-ray tube housing with radiation-absorbent material by wrapping a flexible sheet of the material around the x-ray tube housing and fastening the material in place.

In at least one embodiment, the method of the invention includes fastening the material in place by fastening the material to itself.

In at least one embodiment, the method of the invention includes fastening the material in place by wrapping a belt around a surface of the tube housing opposite the aperture.

In at least one embodiment, the method of the invention includes adhering the material to the tube housing.

Another aspect of the invention is a device for protecting personnel in a vicinity of an operating x-ray machine having an x-ray tube housing that includes a layered radiation-absorbent material configured to cover one or more surfaces of the x-ray tube housing, thereby preventing radiation leaking through the x-ray tube housing from reaching the personnel; a fastener for attaching the material to the surfaces such that the material moves with the x-ray tube housing.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
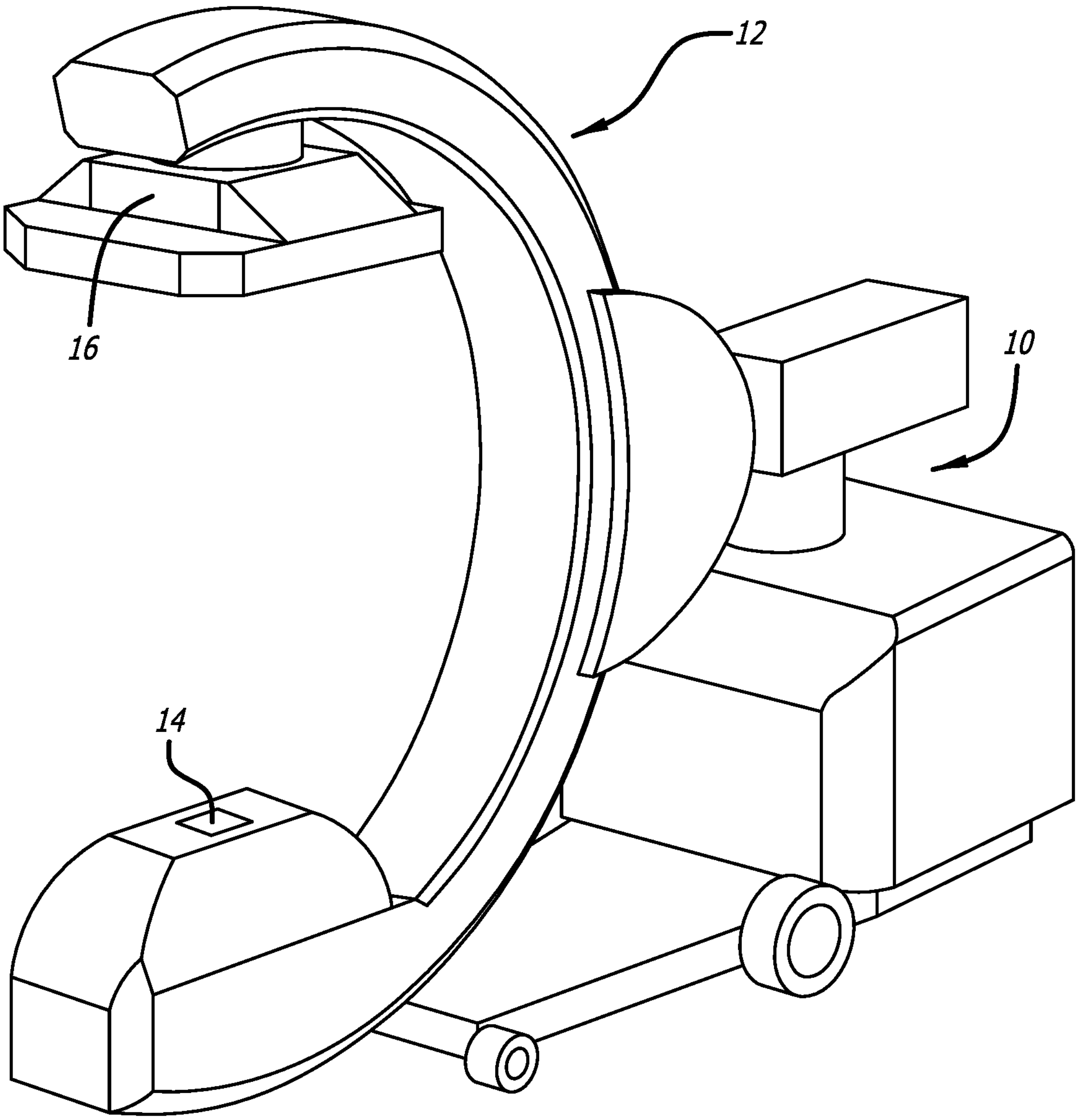
FIG. 1 (Prior Art)
FIG. 1 is a prior art C-arm that exemplifies the devices to which the invention is directed.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring to the Figures, and first to FIG. 1, there is shown an example of a C-arm provided for reference. The C-arm fluoroscope 10 generally includes a C-shaped arm 12 that has an x-ray tube 14 on one end and a flat panel detector 16 opposite the x-ray tube 14.

Figure 2:
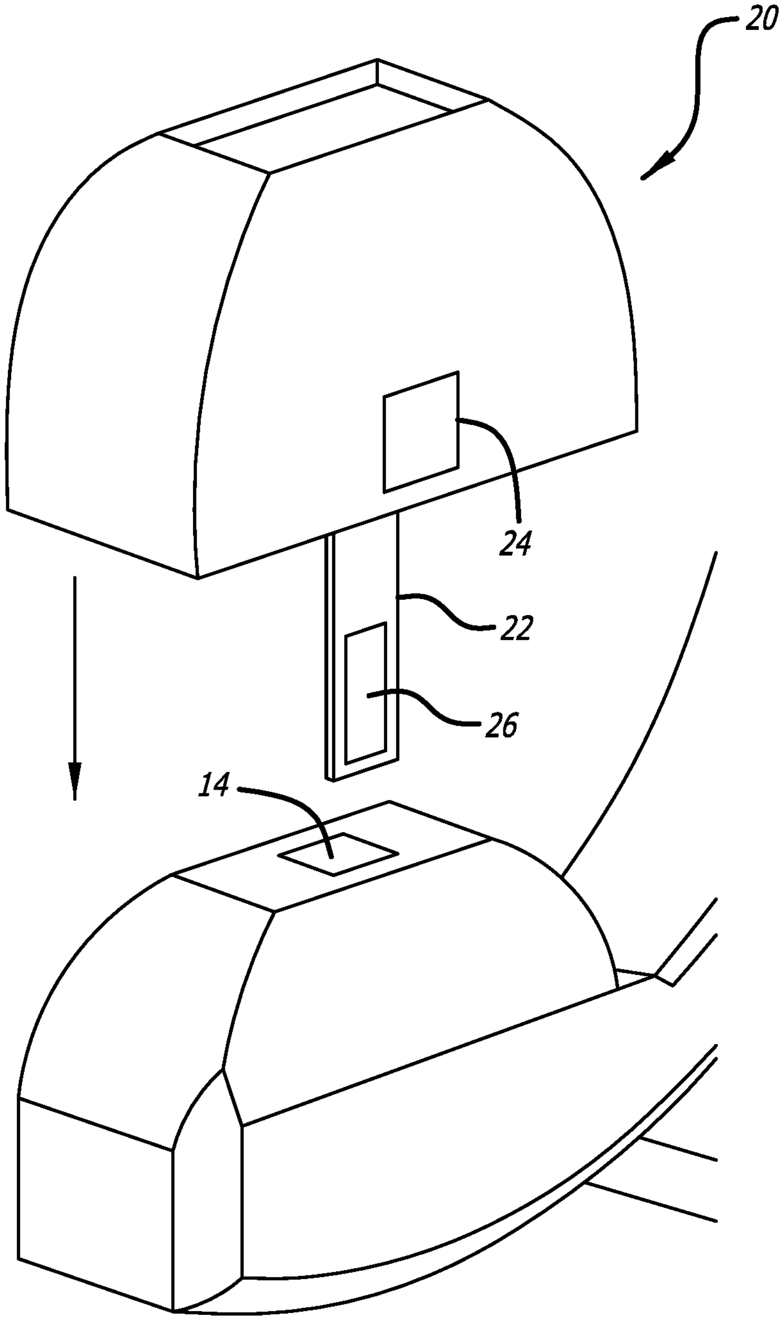
FIG. 2 is a perspective view of an embodiment of the invention.

FIG. 2 shows one embodiment of the invention, which includes a specialized shield 20 made of a radiation-absorbent material that enshrouds the x-ray tube housing 14 and absorbs x-ray photons leaking from the housing and a shielding system around the patient. The amount and type of x-ray absorbing material may be designed to match the quantity and energy of the tube housing photon leak over the area around the patient and the surface of the housing. The tube housing shield 20 rides the tube housing 14 as it rotates about the patient and prevents x-ray photon leak in all directions.

FIG. 2 also demonstrates that the shield 20 is shaped to fit the x-ray tube housing 14 of a given particular C-arm model. For example, if an x-ray tube 14 is cylindrical, the shield 20 will be cylindrical. Also shown is a fastener 22 in the form of a strap. The strap wraps around the bottom of the tube 14 and includes a hook and loop fastener 26 that connects to a corresponding hook and look fastener portion 24 on the shield 20.

Figure 3:
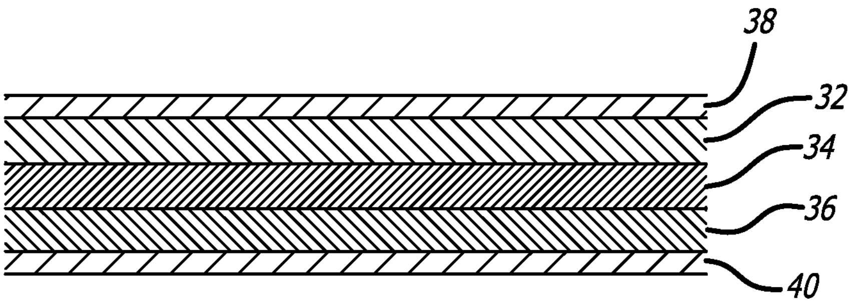
FIG. 3 is a sectional view of an embodiment of a material of the invention.

FIG. 3 shows a cross section of an embodiment of a laminar material structure 30 of the shield 20. In one embodiment, the shield is comprised of one or more layers, such as layers 32, 34 and 36 shown in FIG. 3, of a radio-opaque polymer adhered, bonded, welded or otherwise joined together and formed into a shape that fits over the x-ray tube housing. The polymer layers 32, 34 and 36 are adhered together and to an outer layer 38 and/or inner layer 40 of a flexible protective material such as vinyl. The amount of x-ray photon absorption (and shielding) may be varied based on the thickness of the material. For example, for cardiac x-ray cases, the shielding next to the patient's chest area approximates the absorption equivalence of 1 mm of lead. The shield is reduced to the equivalent of 0.75 mm of lead on the sides of the sled. This fused material may be adhered together into one sheet of material or more than one piece.

Shaping the material to conform to various x-ray tube designs can be accomplished, for example, by heating the polymer and vinyl together. Under heat, the polymer layers fuse together and to the protective layer(s) to provide a very durable material that is easy to cut and form. By staggering the polymer and vinyl cover edges, the material can be fastened into a 3-dimensional shape to enshroud the tube housing, without the need for additional adhesives or sewing. Sewing holes can lead to photon leakage. In one embodiment, a form is constructed having the desired size and dimensions of the x-ray tube housing. The material is heated and applied to the form, or applied to the form and then heated in the alternative, and allowed to cool. The layers of the material become fixed relative to each other and thus retain the desired shape.

The material described above is thus formed into a three-dimensional shape that fits over the x-ray tube housing, allowing an aperture for the x-ray photons to exit to the patient and detector but reducing photon emission from the tube housing.

Figure 4:
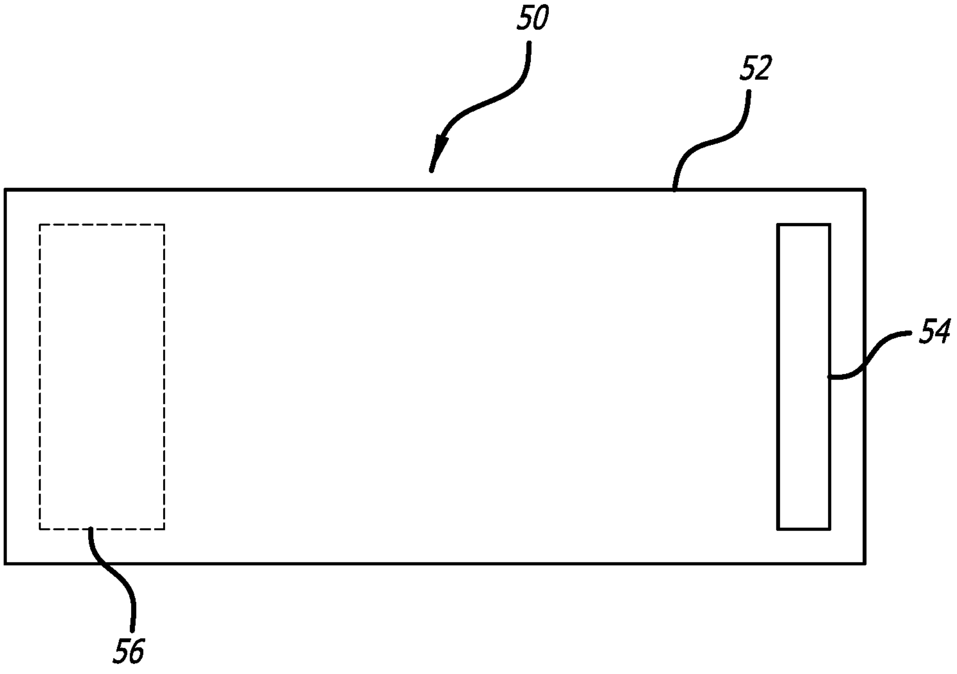
FIG. 4 is a plan view of an embodiment of the invention.

FIG. 4 shows an embodiment 50 that may be used with x-ray tubes having a simpler shape, such as cylindrical or rectangular. The shield 50 is in the form of a flexible band that can be wrapped around the x-ray tube housing and fastened in a number of ways (such as hook and loop fasteners, buckles, zippers and adhesives). FIG. 4 shows components 54 and 56 of a typical hook and loop fastener.

If adhesives are used, it is envisioned that the shield material may be provided in a form that can be shaped and adhered directly to the x-ray tube on a temporary or permanent basis.

Since the level of x-ray photon emission from the tube housing varies by location on the housing, the x-ray absorption characteristics of the cover are adjusted to provide more absorption where there is more leak from the housing. This is accomplished by two principal mechanisms. The first is to create a thicker photon absorbing material at the sites of higher emission (either by using a thicker layer of radio-opaque polymer or by adhering multiple layers together). Thicker material absorbs more photons.

The second method is to use different concentrations of specific x-ray absorbing elements over distinct parts of the tube housing. The reason for this use of differential materials is that the energy of x-ray photons emitted from the tube housing can vary based on where on the tube housing the emission occurs. Higher energies typically occur near the x-ray aperture. The efficiency of photon absorption by x-ray absorbing elements varies with different photon energies. Matching the elemental composition of the x-ray absorbing material to the x-ray emission profile increases efficiency of absorption.

OTHER EMBODIMENTS

X-ray absorption by large atoms is well described. A similar shield could be assembled from the elements alone, without the need for polymer binding. In another embodiment, the shield enshrouding the tube housing can be composed of lead, copper or other metals. The variability in absorption of photons about the housing can be accomplished by varying the thickness of the metal. Additional shielding for different energy level emissions can be accomplished by affixing other elements to the main body of the shield, or by adding polymer loaded with various elements.

Example 1

Data collected using a device of the embodiment 20 of FIG. 1 demonstrates the effectiveness of the invention at reducing radiation leaking through the x-ray tube 14. The data in Table 2 shows the radiation emitted from the tube housing when the specialized shield is mounted to the system.

TABLE 2

| | Right | | | | Caudal | | | | | Left | | | | Cranial | | | | Average |
|---|---|---|---|---|---|---|---|---|---|---|---|---|---|---|---|---|---|---|
| | A | B | C | D | A | B | C | D | E | A | B | C | D | A | B | C | D | 1-4 |
| 1 | 78 | 67 | 78 | 58 | 67 | 68 | 46 | 55 | 43 | 47 | 54 | 44 | 67 | 42 | 49 | 62 | | 58 |
| 2 | 68 | | 39 | 86 | 71 | 87 | 70 | 70 | 61 | 69 | 63 | | | 59 | 63 | 70 | 73 | 68 |

TABLE 2-continued

| | Right | | | | Caudal | | | | | Left | | | | Cranial | | | | Average |
|---|---|---|---|---|---|---|---|---|---|---|---|---|---|---|---|---|---|---|
| | A | B | C | D | A | B | C | D | E | A | B | C | D | A | B | C | D | 1-4 |
| 3 | 55 | | 96 | 97 | 91 | 55 | 47 | 49 | 68 | 71 | 29 | 70 | 92 | | 33 | 38 | 49 | 63 |
| 4 | 56 | 69 | 94 | 67 | 71 | 60 | 50 | 46 | 66 | 41 | 42 | | 78 | | 32 | 48 | 41 | 57 |
| Average 1-4 | | 72 | | | | | 62 | | | | 59 | | | | 50 | | | |

The data reveals that the shielding as designed dramatically reduces the radiation emitted from the tube housing. On average across the entire tube housing, this radiation protection system prevents 85% of the radiation leakage from reaching the patient and the laboratory staff. In the peak radiation leak locations on the tube housing, this radiation protection system reduces the radiation leakage by greater than 95%.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A shield for reducing radiation leakage through an x-ray tube comprising a plurality of radiation-absorbent material layers and at least one protective material layer, wherein the shield is shaped to be secured against and enshroud an x-ray tube housing without obstructing an aperture thereof by thermoforming the plurality of radiation-absorbent material layers and the at least one protective material layer over a form having outer dimensions equal to outer dimensions of the x-ray tube housing, wherein the plurality of radiation-absorbent material layers comprise different concentrations of x-ray absorbing materials over distinct parts of the x-ray tube housing so as to match an x-ray emission profile of x-ray photon energy emitted from the x-ray tube housing.

2. The shield of claim 1 wherein the plurality of radiation-absorbent material layers comprise varying thicknesses of the plurality of radiation-absorbent material layers such that the plurality of radiation-absorbent material layers is thicker in areas on the x-ray tube housing having higher photon emission.

3. The shield of claim 1 wherein said shield further includes an adhesive for adhering the shield to an x-ray tube housing.

4. The shield of claim 1, further comprising a fastener made from a flexible material and adapted to be wrapped around the x-ray tube housing and fastened to the shield.

5. The shield of claim 4 wherein said fastener comprises a hook and loop fastener.

6. A method of reducing radiation exposure to health care workers present during an x-ray procedure, comprising:

covering surfaces of an x-ray tube housing with a shield comprising a plurality of radiation-absorbent material layers and at least one protective material layer to an x-ray tube housing so as to entirely cover a plurality of sides and an upper end of the x-ray tube housing without obstructing an aperture thereof by forming the plurality of radiation-absorbent material layers and the at least one protective material layer into a shape that is configured to enshroud the x-ray tube housing while not obstructing an x-ray aperture thereof and fastening the shield to the x-ray tube housing, wherein forming the plurality of radiation-absorbent material layers and the at least one protective material layer into a shape that is configured to enshroud the x-ray tube housing while not obstructing an x-ray aperture thereof comprises heating the plurality of radiation-absorbent material layers, applying the plurality of radiation-absorbent material layers to a form having the shape and allowing polymer of the plurality of radiation-absorbent material layers to fuse together, wherein the plurality of radiation-absorbent material layers comprise different concentrations of x-ray absorbing materials over distinct parts of the x-ray tube housing so as to match an x-ray emission profile of x-ray photon energy emitted from the x-ray tube housing.

7. The method of claim 6 wherein covering surfaces of the x-ray tube housing with the shield comprises wrapping a flexible sheet of the shield around the x-ray tube housing and fastening the shield in place.

8. The method of claim 7 wherein fastening the shield in place comprises fastening the shield to itself.

9. The method of claim 7 wherein fastening the shield in place comprises wrapping a belt around a surface of the x-ray tube housing opposite the aperture.

10. The method of claim 7 wherein fastening the shield in place comprises adhering the shield to the x-ray tube housing.

11. A shield for protecting personnel in a vicinity of an operating x-ray machine having an x-ray tube housing comprising:

a plurality of radiation-absorbent material layers configured to cover at least at least one surface of the x-ray tube housing without obstructing an aperture thereof, thereby preventing radiation leaking through the x-ray tube housing from reaching the personnel;

wherein the plurality of radiation-absorbent material layers comprise different concentrations of x-ray absorbing materials over distinct parts of the x-ray tube housing so as to match an x-ray emission profile of x-ray photon energy emitted from the x-ray tube housing; and a fastener for attaching the plurality of radiation-absorbent material layers to the at least one surface of the x-ray tube housing such that the plurality of radiation-absorbent material layers moves with the x-ray tube housing, wherein the fastener comprises a first end fixedly attached to a first side of the shield and a second end removably attached to a second side of the shield, wherein the fastener wraps around a bottom of the x-ray tube housing.

12. The shield of claim 11 wherein the plurality of radiation-absorbent material layers is constructed to have varying x-ray absorption capabilities that vary in accordance with a varying photon emission rate of the x-ray tube housing.

13. The shield of claim 12 wherein the varying x-ray absorption capabilities result from varying thicknesses of the plurality of radiation-absorbent material layers such that the plurality of radiation-absorbent material layers is thicker in areas on the x-ray tube housing having higher photon emission.

14. The shield of claim 12 wherein the varying x-ray absorption capabilities result from varying concentrations of radiation-absorbent elements used in making the plurality of radiation-absorbent material layers such that the plurality of radiation-absorbent material layers is non-homogenous, having different elements that correspond to the varying photon emission rate of the x-ray tube housing.

* * * * *